(12) United States Patent
Yoon et al.

(10) Patent No.: US 9,459,138 B2
(45) Date of Patent: Oct. 4, 2016

(54) ULTRASONIC TRANSDUCER, AND ULTRASONIC WAVE GENERATING APPARATUS AND ULTRASONIC SYSTEM INCLUDING THE SAME

(71) Applicant: SAMSUNG ELECTRONICS CO., LTD., Suwon-si (KR)

(72) Inventors: Yong-seop Yoon, Seoul (KR); Sung-chan Kang, Hwaseong-si (KR); Yong-hyup Kim, Seoul (KR); Mi-ae Park, Seoul (KR); Jai-ick Yoh, Seoul (KR); Seok-hwan Lee, Seoul (KR); Woon-bae Kim, Seoul (KR); Jong-seok Kim, Hwaseong-si (KR); Hye-lynn Song, Seoul (KR); Eui-yun Jang, Seoul (KR)

(73) Assignees: SAMSUNG ELECTRONICS CO., LTD., Suwon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 111 days.

(21) Appl. No.: 13/955,875

(22) Filed: Jul. 31, 2013

(65) Prior Publication Data
US 2014/0033822 A1    Feb. 6, 2014

(30) Foreign Application Priority Data
Aug. 1, 2012  (KR) .................. 10-2012-0084592

(51) Int. Cl.
  *G01H 9/00*  (2006.01)
  *B06B 1/00*  (2006.01)
  *A61B 8/00*  (2006.01)

(52) U.S. Cl.
  CPC ............. *G01H 9/00* (2013.01); *A61B 8/4483* (2013.01); *B06B 1/00* (2013.01)

(58) Field of Classification Search
  CPC ......... G01H 9/00; A61B 8/4483; B06B 1/00
  USPC .......................................... 73/632, 606, 643
  See application file for complete search history.

(56) References Cited

U.S. PATENT DOCUMENTS

| 4,137,991 A * | 2/1979 | Melcher .............. G10K 15/046 181/142 |
| 4,408,213 A * | 10/1983 | Bell ..................... G11B 7/2578 346/135.1 |

(Continued)

FOREIGN PATENT DOCUMENTS

| GB | WO 9735179 A1 * | 9/1997 | ......... A61B 5/14542 |
| KR | 10-0817615 B1 | 3/2008 | |

(Continued)

OTHER PUBLICATIONS

A High Frequency Ultrasound Array Element Using Thermoelastic Expansion in PDMS, 2001 IEEE, by Buma et al.*

(Continued)

*Primary Examiner* — Laura Martin
*Assistant Examiner* — Suman K Nath
(74) *Attorney, Agent, or Firm* — Sughrue Mion, PLLC (57) ABSTRACT

An ultrasonic transducer, and an ultrasonic wave generating apparatus and an ultrasonic system including the same. The ultrasonic transducer includes a light-absorbing layer configured to absorb light incident on the light-absorbing layer and to generate heat based on the absorbed light; and a thermoelastic layer which is disposed on the light-absorbing layer and which is configured to thermally expand based on the heat to generate ultrasonic waves.

17 Claims, 4 Drawing Sheets

(56) References Cited

U.S. PATENT DOCUMENTS

| | | | |
|---|---|---|---|
| 4,513,384 A * | 4/1985 | Rosencwaig | 702/170 |
| 6,266,857 B1 | 7/2001 | Corbett, III et al. | |
| 6,466,806 B1 * | 10/2002 | Geva et al. | 600/310 |
| 6,711,954 B2 | 3/2004 | Drake, Jr. | |
| 6,784,000 B2 | 8/2004 | Sikora et al. | |
| 7,286,241 B2 | 10/2007 | Drake, Jr. | |
| 8,064,488 B2 | 11/2011 | Drake, Jr. et al. | |
| 2002/0037599 A1 * | 3/2002 | Ishida | G03F 7/091 438/29 |
| 2005/0201575 A1 * | 9/2005 | Koshida | H04R 23/002 381/164 |
| 2009/0097012 A1 | 4/2009 | Gardner | |
| 2010/0033723 A1 * | 2/2010 | Thundat | G01N 29/2418 356/432 |
| 2010/0242612 A1 * | 9/2010 | Sano | B06B 1/0292 73/632 |
| 2011/0197957 A1 * | 8/2011 | Yoshikawa | H01L 31/076 136/255 |
| 2014/0112107 A1 * | 4/2014 | Guo | B06B 1/00 367/191 |
| 2014/0190550 A1 * | 7/2014 | Loh | H01L 51/445 136/244 |

FOREIGN PATENT DOCUMENTS

| | | | | |
|---|---|---|---|---|
| KR | 10-2008-0046259 A | 5/2008 | | |
| KR | 10-2010-0118633 A | 11/2010 | | |
| KR | 10-0993989 B1 | 11/2010 | | |
| KR | 10-2011-0010113 A | 1/2011 | | |
| KR | 10-1148750 B1 | 5/2012 | | |
| SG | WO 2013022405 A1 * | 2/2013 | | H01L 27/302 |
| WO | WO 2013022405 A1 * | 2/2013 | | H01L 31/06 |

OTHER PUBLICATIONS

A High Frequency Ultrasound Array Element Using Thermoelastic Expansion in PDMS, 2001 IEEE, Buma.*

A High Frequency Ultrasound Array Element Using Thermoelastic Expansion in PDMS, 2001 IEEE.*

Hyoung Won Baac, et al; "Carbon Nanotube Composite Optoacoustic Transmitters for Strong and High Frequency Ultrasound Generation"; Applied Physics letters, 2010, vol. 97, No. 234104, 3 pgs.

* cited by examiner

ULTRASONIC TRANSDUCER, AND ULTRASONIC WAVE GENERATING APPARATUS AND ULTRASONIC SYSTEM INCLUDING THE SAME

CROSS-REFERENCE TO RELATED APPLICATIONS

This application claims the benefit of Korean Patent Application No. 10-2012-0084592, filed on Aug. 1, 2012, in the Korean Intellectual Property Office, the disclosure of which is incorporated herein in its entirety by reference.

BACKGROUND

1. Field

The present disclosure relates to ultrasonic transducers that generate ultrasonic waves by using light, and ultrasonic wave generating apparatuses and ultrasonic systems including the ultrasonic transducers.

2. Description of the Related Art

When a laser beam is emitted towards a liquid material or a solid material, the material absorbs light to instantly generate heat, and thus generates acoustic waves due to a thermoelastic phenomenon.

Since an ultrasonic wave generating apparatus using a laser beam may more easily generate high frequency ultrasonic waves and generate ultrasonic waves over a wider range of frequencies than a conventional ultrasonic wave generating apparatus using a piezoelectric element, the ultrasonic wave generating apparatus using the laser beam may obtain a higher-resolution image.

Ultrasonic waves generated in this manner are used for analysis of materials, non-destructive testing, photoacoustic tomography, etc.

SUMMARY

According to exemplary embodiments, there are provided ultrasonic transducers that generate ultrasonic waves by using light, and ultrasonic wave generating apparatuses and ultrasonic systems including the ultrasonic transducers.

Further, according to exemplary embodiments, there are provided ultrasonic transducers that efficiently generate ultrasonic waves by using a light-absorbing layer and a thermoelastic layer, and ultrasonic wave generating apparatuses and ultrasonic systems including the ultrasonic transducers.

Additional aspects will be set forth in part in the description which follows and, in part, will be apparent from the description, or may be learned by practice of the exemplary embodiments.

According to an aspect of an exemplary embodiment, an ultrasonic transducer includes: a light-absorbing layer configured to absorb light incident on the light-absorbing layer and to generate heat based on the absorbed light; and a thermoelastic layer which is disposed on the light-absorbing layer and which is configured to thermally expand based on the heat to generate ultrasonic waves.

The light may be a pulsed laser beam.

A pulse width of the pulsed laser beam may be nano or pico-sized.

An absorption coefficient of the light-absorbing layer may be higher than an absorption coefficient of the thermoelastic layer.

A reflection coefficient of the light-absorbing layer may be lower than a reflection coefficient of the thermoelastic layer.

The light-absorbing layer may include graphene.

The light-absorbing layer may include a reduced graphene oxide.

A thickness of the light-absorbing layer may range from about 10 nm to about 100 nm.

An absorption coefficient of the light-absorbing layer may increase as the thickness of the light-absorbing layer increases.

The thermoelastic layer may include at least one of a metal material, a semiconductor material, a carbon-based material, and a polymer material.

The thermoelastic layer may be formed as a thin film.

The ultrasonic transducer may further include a substrate that is disposed on the light-absorbing layer.

The substrate may be transparent.

The substrate may be disposed on a surface of the light-absorbing layer facing another surface of the light-absorbing layer on which the thermoelastic layer is disposed.

According to another aspect of an exemplary embodiment, an ultrasonic wave generating apparatus includes an ultrasonic transducer including a light-absorbing layer configured to absorb light incident on the light-absorbing layer and to generate heat based on the absorbed light, and a thermoelastic layer which is disposed on the light-absorbing layer and which is configured to thermally expand based on the heat to generate ultrasonic waves, and a light source that generates the light.

The light source, the light-absorbing layer, and the thermoelastic layer may be sequentially disposed on a path on which the light travels.

The ultrasonic wave generating apparatus may further include at least one of: a matching unit configured to match an acoustic wave impedance of the ultrasonic waves to an acoustic wave impedance of an object; a sound-absorbing unit configured to absorb ultrasonic waves traveling away from the object from among the ultrasonic waves; and an acoustic lens configured to focus ultrasonic waves traveling toward the object from among the ultrasonic waves.

The ultrasonic wave generating apparatus may be implemented as an ultrasonic probe.

According to another aspect of an exemplary embodiment, an ultrasonic system includes: a processor configured to process an electrical signal corresponding to an echo signal of ultrasonic waves generated by an ultrasonic transducer including a light-absorbing layer configured to absorb light incident on the light-absorbing layer and to generate heat based on the absorbed light, and a thermoelastic layer which is disposed on the light-absorbing layer and which is configured to thermally expand based on the heat to generate the ultrasonic waves, the processor being further configured to generate an image based on the electrical signal; and a display unit configured to display the image.

The ultrasonic system may further include a receiving unit configured to receive the echo signal from an object to which the ultrasonic waves are emitted.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

The exemplary embodiments will now be described more fully with reference to the accompanying drawings, in which exemplary embodiments are shown.

A laser-induced ultrasonic wave generating apparatus (hereinafter, also referred to as an ultrasonic wave generating apparatus) is an apparatus that induces ultrasonic waves by using a laser beam, and determines whether there is a tumor or the like in an object, e.g., a patient's body, by using the ultrasonic waves. The ultrasonic wave generating apparatus includes an ultrasonic transducer that induces ultrasonic waves from a laser beam. Ultrasonic waves are generated when the absorbed light is converted into pressure.

Figure 1:
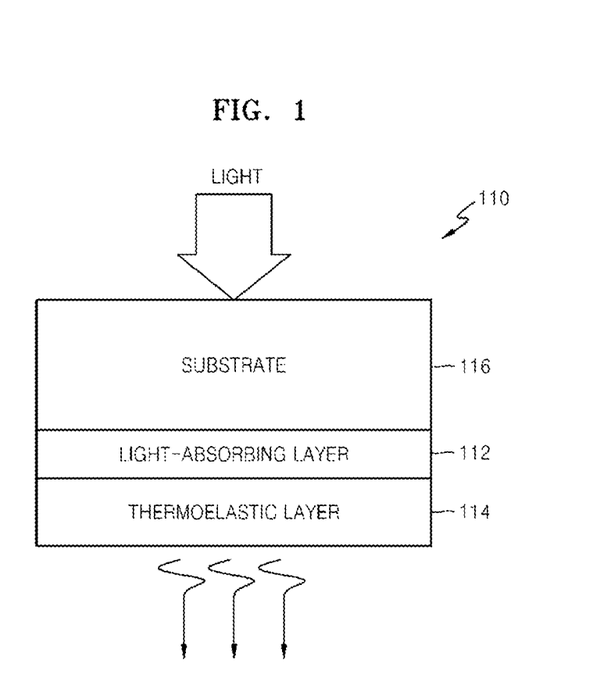
FIG. 1 is a cross-sectional view illustrating an ultrasonic transducer according to an exemplary embodiment.

FIG. 1 is a cross-sectional view illustrating an ultrasonic transducer 110 according to an exemplary embodiment.

Referring to FIG. 1, the ultrasonic transducer 110 includes a light-absorbing layer 112 that absorbs light and generates heat based on the absorbed light, and then transmits the heat, and a thermoelastic layer 114 that is disposed on the light-absorbing layer 112 and is thermally expanded by the heat transmitted from the light-absorbing layer 112 to generate ultrasonic waves. The ultrasonic transducer 110 may further include a substrate 116 that supports the light-absorbing layer 112 and the thermoelastic layer 114.

Light incident on the ultrasonic transducer 110 may be a laser beam. The laser beam may be a pulsed laser beam, and a pulse width of the laser beam may be nano or pico-sized, although is not limited thereto. Induced ultrasonic waves increase as the pulse width of the laser beam decreases and a pulse fluence of the laser beam increases.

The substrate 116 is disposed on a surface of the light-absorbing layer 112 opposite to a surface of the light-absorbing layer 112 on which the thermoelastic layer 114 is disposed, and supports the light-absorbing layer 112 and the thermoelastic layer 114. For example, the substrate 116 may be disposed on a surface of the light-absorbing layer 112 facing a surface of the light-absorbing layer 112 on which the thermoelastic layer 114 is disposed. The substrate 116 may be formed of a material having a high transmittance so that light may be incident on the light-absorbing layer 112 without loss. For example, the substrate 116 may be transparent. The substrate 116 may be formed of quartz, fused silica, or glass, although is not limited thereto and may also be formed of other materials.

The light-absorbing layer 112 may be formed of a material having a high absorption coefficient and high thermal conductivity. For example, an absorption coefficient of the light-absorbing layer 112 may be higher than an absorption coefficient of the thermoelastic layer 114, and a reflection coefficient of the light-absorbing layer 112 may be lower than a reflection coefficient of the thermoelastic layer 114. The light-absorbing layer 112 may be formed of a material having excellent mechanical durability. The light-absorbing layer 112 may include graphene. Graphene is an allotrope of carbon having a structure which is one-atom-thick planar sheets of $sp^2$-bonded carbon atoms that are densely packed in a honeycomb crystal lattice. Graphene is a material that is structurally and chemically very stable and has high thermal conductivity and high efficiency with respect to absorbing light and converting light into heat. In particular, according to exemplary embodiments, the light-absorbing layer 112 may be formed of a reduced graphene oxide.

An absorption coefficient of the light-absorbing layer 112 decreases as a thickness of the light-absorbing layer 112 decreases, and a thermal conductivity of the light-absorbing layer 112 decreases as a thickness of the light-absorbing layer 112 increases. Accordingly, a thickness of the light-absorbing layer 112 may be determined within an appropriate range in which a high absorption coefficient and high thermal conductivity are ensured. A thickness of the light-absorbing layer 112 may range from about 10 nm to about 100 nm.

The thermoelastic layer 114 may be formed of a material that may be easily expanded and contracted due to heat transmitted from the light-absorbing layer 112. That is, the thermoelastic layer 114 may be formed of a material having a high thermal expansion coefficient. The thermoelastic layer 114 may be formed as a thin film in order to facilitate thermal expansion and contraction. A thickness of the thermoelastic layer 114 may be about several μm, although is not limited thereto and may greater or less than several μm. According to exemplary embodiments, the thermoelastic layer 114 may be formed of at least one of a metal material such as chromium (Cr), titanium (Ti), gold (Au), or aluminum (Al), a carbon-based material such as carbon nanotubes (CNTs), a semiconductor material such as silicon, and a polymer material such as polydimethylsiloxane (PDMS).

The ultrasonic transducer 110 may convert light into ultrasonic waves as follows. When light having an energy density I (x, y, z, t) is emitted towards the light-absorbing layer 112, the light-absorbing layer 112 generates heat H based on the light as defined by Equation 1:

$$H = (1-R) \cdot I \cdot \mu e^{\mu z} \quad \text{(Equation 1)},$$

where R is a reflection coefficient of the light-absorbing layer 112, μ is an absorption coefficient of the light-absorbing layer 112, and z is a distance in a direction perpendicular to a surface of the light-absorbing layer 112 on which the light is incident.

The heat H is transmitted to the thermoelastic layer 114. Since loss occurs when the heat H is transmitted from the light-absorbing layer 112 to the thermoelastic layer 114, the light-absorbing layer 112 may be formed of a material having a high heat transfer rate. An example of a material having a high heat transfer rate includes graphene.

A temperature T of the thermoelastic layer 114 receiving the heat H from the light-absorbing layer 112 changes according to Equation 2. In Equation 2, it is assumed that the heat H is transmitted from the light-absorbing layer 112 to the thermoelastic layer 114 without loss. If loss occurs, heat actually generated in the thermoelastic layer 114 may be less than the heat H in Equation 2:

$$\frac{k}{C^2} \frac{\partial^2 T}{\partial t^2} + \rho C_P \frac{\partial T}{\partial t} = \nabla (k \cdot \nabla T) + H, \quad \text{(Equation 2)}$$

where k is a thermal conductivity of the thermoelastic layer 114, C is a heat propagation speed in the thermoelastic layer 114, ρ is a density of the thermoelastic layer 114, and $C_P$ is a specific heat of the thermoelastic layer 114.

Due to the change in the temperature T, a volume V of the thermoelastic layer 114 changes according to Equation 3:

$$\frac{\partial^2}{\partial t^2}\left(\frac{dV}{V}\right) = \beta \frac{\partial^2 T}{\partial t^2}, \qquad \text{(Equation 3)}$$

where β is a thermal expansion coefficient of the thermoelastic layer 114.

Due to the change in the volume V, ultrasonic waves having a pressure P are generated according to Equation 4:

$$\frac{1}{\rho}\left(\nabla^2 - \frac{1}{V_S^2}\frac{\partial^2}{\partial t^2}\right)P = -\frac{\partial^2}{\partial t^2}\left(\frac{dV}{V}\right), \qquad \text{(Equation 4)}$$

where $v_s$ is a speed of the ultrasonic waves.

As such, since the ultrasonic transducer 110 has a dual-layer structure including a layer that absorbs light and a layer that generates ultrasonic waves, the ultrasonic transducer 110 may generate ultrasonic waves even when the ultrasonic transducer 110 absorbs light having low energy. That is, since a layer formed of a material having a high absorption coefficient and a low reflection coefficient absorbs light and a layer formed of a material having a high thermoelastic constant generates ultrasonic waves, according to exemplary embodiments, the efficiency in generating ultrasonic waves may be maximized.

Figure 2:
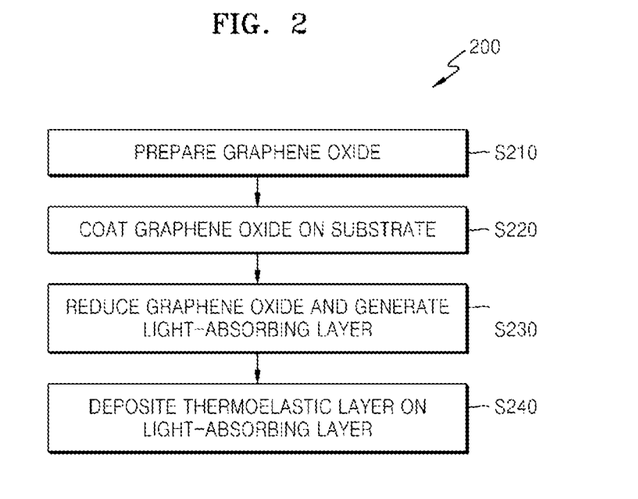
FIG. 2 is a flowchart illustrating a method of manufacturing the ultrasonic transducer including a reduced graphene oxide, according to an exemplary embodiment.

FIG. 2 is a flowchart illustrating a method of manufacturing the ultrasonic transducer 110 including a reduced graphene oxide, according to an exemplary embodiment.

In operation S210, a graphene oxide is prepared. For example, graphite and potassium permanganate are mixed and sulfuric acid is added to obtain a suspension. Water and hydrogen peroxide are successively added to the suspension. When the suspension turns from brown to yellow, the suspension is filtered to obtain a graphene oxide.

In operation S220, the graphene oxide may be coated on the substrate 116 by using spin coating or another technique. The substrate 116 may be a transparent substrate having a high transmittance. In operation S230, the substrate 116 on which the graphene oxide is coated may be annealed to reduce the graphene oxide and generate the light-absorbing layer 112.

In operation S240, the thermoelastic layer 114, for example, an Al thin film, may be deposited on the substrate 116 on which the reduced graphene oxide is coated by using e-beam evaporation or another technique.

Figure 3:
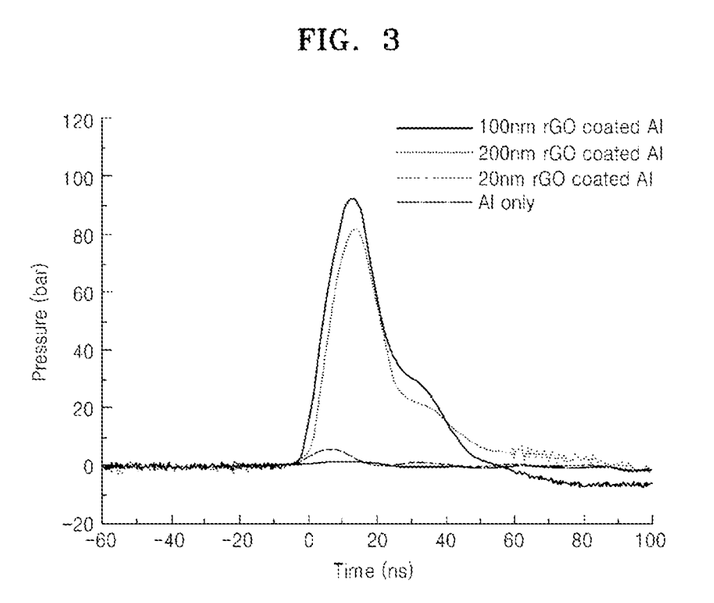
FIG. 3 is a graph illustrating a result obtained by measuring performances of ultrasonic transducers.

FIG. 3 is a graph illustrating a result obtained by measuring performances of ultrasonic transducers. A light-absorbing layer was formed of a reduced graphene oxide and a thermoelastic layer was formed as an Al thin film. An ultrasonic transducer including only a thermoelastic layer without a light-absorbing layer was manufactured, and three ultrasonic transducers including thermoelastic layers deposited on light-absorbing layers having thicknesses of 20 nm, 200 nm, and 100 nm, according to exemplary embodiments, were manufactured. Light having an energy density of 14 mJ/cm² was emitted towards each of the ultrasonic transducers. A relationship between pressure and time for each of the ultrasonic transducers was obtained as shown in FIG. 3.

Referring to FIG. 3, the ultrasonic transducer including only the thermoelastic layer did not generate ultrasonic waves from the light having an energy density of 14 mJ/cm². However, the three ultrasonic transducers including the light-absorbing layers generated ultrasonic waves. Also, it was found that as a thickness of a light-absorbing layer increased, more ultrasonic waves were generated. However, when a light-absorbing layer exceeded a predetermined thickness, ultrasonic waves were reduced. Therefore, according to exemplary embodiments, ultrasonic waves may be generated from light more easily when a thermoelastic layer is deposited on a light-absorbing layer having an optimum thickness.

Figure 4:
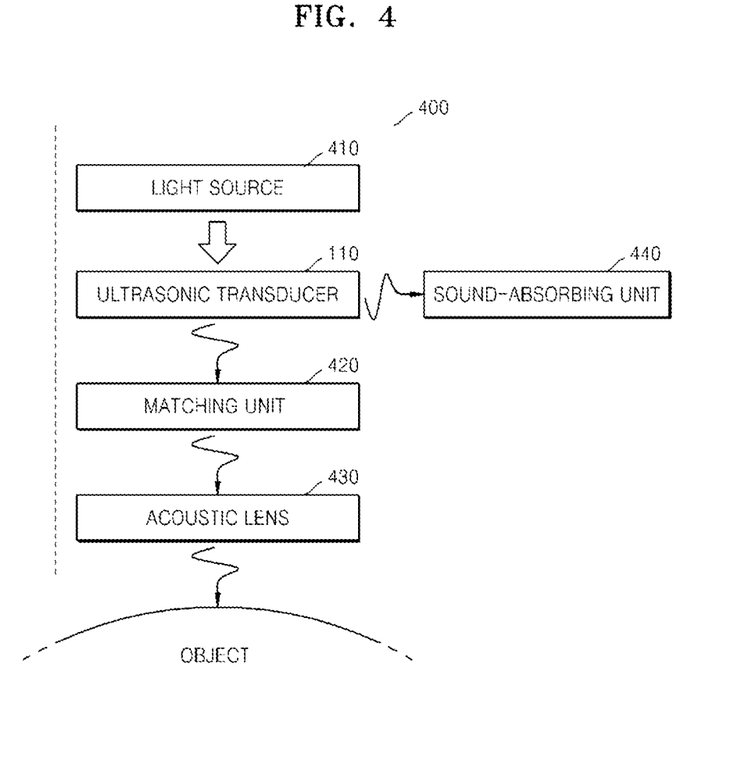
FIG. 4 is a block diagram illustrating an ultrasonic wave generating apparatus including the laser-induced ultrasonic transducer of FIG. 1, according to an exemplary embodiment.

FIG. 4 is a block diagram illustrating an ultrasonic wave generating apparatus 400 including the ultrasonic transducer 110 of FIG. 1, according to an exemplary embodiment.

Referring to FIG. 4, the ultrasonic wave generating apparatus 400 may include a light source 410 that emits light to the ultrasonic transducer 110, and the ultrasonic transducer 110 that converts the light into ultrasonic waves. The light source 410 may be disposed such that light is incident on the light-receiving layer 112 of the ultrasonic transducer 110. For example, the light source 410, the light-absorbing layer 112, and the thermoelastic layer 114 may be sequentially disposed on a path through which light travels.

The light source 410 may generate a pulsed laser beam. A pulse width of the laser beam may be nano or pico-sized, although is not limited thereto. The light source 410 and the ultrasonic transducer 110 may be disposed in the same housing, and the ultrasonic wave generating apparatus 400 may be implemented as an ultrasonic probe.

The ultrasonic wave generating apparatus 400 may further include a matching unit 420 that matches an acoustic impedance of ultrasonic waves generated by the ultrasonic transducer 110 to an acoustic impedance of the object. The matching unit 420 may change the acoustic impedance of the ultrasonic waves generated by the ultrasonic transducer 110 in a stepwise manner to make the acoustic impedance of the ultrasonic waves more closely resemble the acoustic impedance of the object. Hence, the matching unit 420 may be disposed on a front surface of the ultrasonic transducer 110. The front surface of the ultrasonic transducer 110 may be a surface closest to the object from among surfaces of the ultrasonic transducer 110 when ultrasonic waves are emitted to the object, and a rear surface of the ultrasonic transducer 110 may be a surface opposite to the front surface. The matching unit 420 may extend along the front surface of the ultrasonic transducer 110, but the present exemplary embodiment is not limited thereto. According to exemplary embodiments, the matching unit 420 may be formed of PDMS (polydimethylsiloxane), although is not limited thereto.

The ultrasonic wave generating apparatus 400 may further include a sound-absorbing unit 440 that absorbs ultrasonic waves traveling away from the object and an acoustic lens 430 that focuses ultrasonic waves traveling toward the object.

Figure 5:
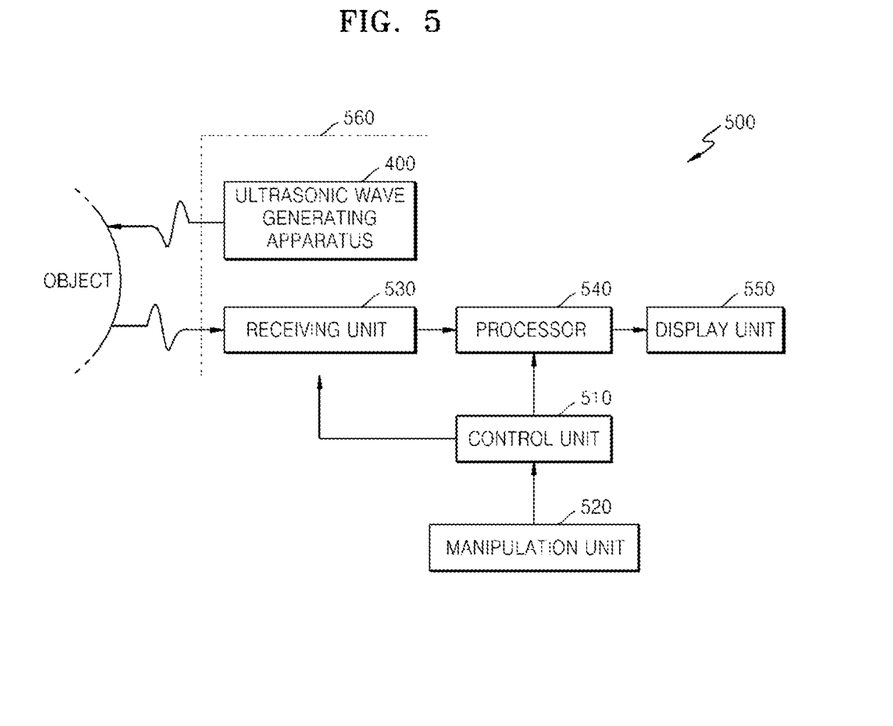
FIG. 5 is a block diagram illustrating an ultrasonic system for generating an ultrasonic image by using the ultrasonic wave generating apparatus of FIG. 4, according to an exemplary embodiment.

FIG. 5 is a block diagram illustrating an ultrasonic system 500 for generating an ultrasonic image by using the ultrasonic wave generating apparatus 400 of FIG. 4, according to an exemplary embodiment.

Referring to FIG. 5, the ultrasonic system 500 may include a control unit 510 that controls an overall operation of the ultrasonic system 500, a manipulation unit 520 that receives a command from a user, the ultrasonic wave generating apparatus 400 that generates ultrasonic waves by using a laser beam, a receiving unit 530 that receives an echo signal of the ultrasonic waves from the object, a processor 540 that performs signal processing on the ultrasonic waves and generates an image, and a display unit 550 that displays the image.

The ultrasonic wave generating apparatus 400 and the receiving unit 530 may be disposed in the same housing. For example, the ultrasonic wave generating apparatus 400 and the receiving unit 530 may be disposed in an ultrasonic probe 560.

The receiving unit 530 may include a transducer that converts ultrasonic waves into an electrical signal. According to exemplary embodiments, examples of the transducer may include a piezoelectric micromachined ultrasonic transducer (pMUT) that converts ultrasonic waves into an electrical signal through oscillation, a capacitive micromachined ultrasonic transducer (cMUT), a magnetic micromachined ultrasonic transducer (mMUT), and an optical ultrasonic detector.

The electrical signal obtained by the receiving unit 530 may be an analog signal. The processor 540 may generate an image by converting the analog signal applied from the receiving unit 530 into a digital signal. According to exemplary embodiments, examples of the image generated by the processor 540 may include a brightness (B) mode image, a Doppler (D) mode image, a color Doppler (C) mode image, an elastic image, and a three-dimensional (3D) image.

A laser-induced ultrasonic transducer according to exemplary embodiments may increase ultrasonic pressure even when a laser beam having low energy is used.

Also, since energy per unit pulse of a laser beam may be reduced and thus a pulse repetition rate may be increased, a time taken to obtain an image may be reduced and a high resolution image may be obtained.

Since characteristics of ultrasonic waves vary according to types of a light-absorbing layer and a thermoelastic layer, characteristics of ultrasonic waves may be adjusted according to an object to be diagnosed.

It is to be understood that the foregoing is illustrative of exemplary embodiments and is not to be construed as limited to the specific exemplary embodiments disclosed, and that modifications to the disclosed exemplary embodiments, as well as other exemplary embodiments, are intended to be included within the scope of the appended claims. Exemplary embodiments are defined by the following claims, with all changes, equivalents, and substitutes of the claims to be included therein.

What is claimed is:

1. An ultrasonic transducer comprising:
a light-absorbing layer configured to absorb light incident on the light-absorbing layer and to generate heat based on the absorbed light; and
a thermoelastic layer which is disposed on the light-absorbing layer, the thermoelastic layer being formed of a material different from a material of the light-absorbing layer, the thermoelastic layer being configured to thermally expand based on the heat to generate ultrasonic waves,
wherein an absorption coefficient of the light-absorbing layer is higher than an absorption coefficient of the thermoelastic layer,
wherein a reflection coefficient of the light-absorbing layer is lower than a reflection coefficient of the thermoelastic layer, and
wherein the light-absorbing layer comprises graphene.

2. The ultrasonic transducer of claim 1, wherein the light is a pulsed laser beam.

3. The ultrasonic transducer of claim 2, wherein a pulse width of the pulsed laser beam is nano or pico-sized.

4. The ultrasonic transducer of claim 1, wherein the light-absorbing layer comprises a reduced graphene oxide.

5. The ultrasonic transducer of claim 1, wherein a thickness of the light-absorbing layer ranges from about 10 nm to about 100 nm.

6. The ultrasonic transducer of claim 5, wherein an absorption coefficient of the light-absorbing layer increases as the thickness of the light-absorbing layer increases.

7. The ultrasonic transducer of claim 1, wherein the thermoelastic layer comprises at least one of a metal material, a semiconductor material, a carbon-based material, and a polymer material.

8. The ultrasonic transducer of claim 1, wherein the thermoelastic layer is formed as a thin film.

9. The ultrasonic transducer of claim 1, further comprising a substrate that is disposed on the light-absorbing layer.

10. The ultrasonic transducer of claim 9, wherein the substrate is transparent.

11. The ultrasonic transducer of claim 9, wherein the substrate is disposed on a surface of the light-absorbing layer facing another surface of the light-absorbing layer on which the thermoelastic layer is disposed.

12. An ultrasonic wave generating apparatus comprising:
an ultrasonic transducer, comprising:
a light-absorbing layer configured to absorb light incident on the light-absorbing layer and to generate heat based on the absorbed light, and
a thermoelastic layer which is disposed on the light-absorbing layer, the thermoelastic layer being formed of a material different from a material of the light-absorbing layer, the thermoelastic layer being configured to thermally expand based on the heat to generate ultrasonic waves; and
a light source that generates the light,
wherein an absorption coefficient of the light-absorbing layer is higher than an absorption coefficient of the thermoelastic layer,
wherein a reflection coefficient of the light-absorbing layer is lower than a reflection coefficient of the thermoelastic layer, and
wherein the light-absorbing layer comprises graphene.

13. The ultrasonic wave generating apparatus of claim 12, wherein the light source, the light-absorbing layer, and the thermoelastic layer are sequentially disposed on a path on which the light travels.

14. The ultrasonic wave generating apparatus of claim 12, further comprising at least one of:
a matching unit configured to match an acoustic wave impedance of the ultrasonic waves to an acoustic wave impedance of an object;
a sound-absorbing unit configured to absorb ultrasonic waves traveling away from the object from among the ultrasonic waves; and
an acoustic lens configured to focus ultrasonic waves traveling toward the object from among the ultrasonic waves.

15. The ultrasonic wave generating apparatus of claim 12, wherein the ultrasonic wave generating apparatus is implemented as an ultrasonic probe.

16. An ultrasonic system comprising:
a processor configured to process an electrical signal corresponding to an echo signal of ultrasonic waves generated by an ultrasonic transducer comprising a light-absorbing layer configured to absorb light incident on the light-absorbing layer and to generate heat based on the absorbed light, and a thermoelastic layer which is disposed on the light-absorbing layer, the thermoelastic layer being formed of a material different from a material of the light-absorbing layer, the thermoelastic layer being configured to thermally expand based on the heat to generate the ultrasonic waves, the processor being further configured to generate an image based on the electrical signal; and a display unit configured to display the image, wherein an absorption coefficient of the light-absorbing layer is higher than an absorption coefficient of the thermoelastic layer, wherein a reflection coefficient of the light-absorbing layer is lower than a reflection coefficient of the thermoelastic layer, and wherein the light-absorbing layer comprises graphene.

17. The ultrasonic system of claim 16, further comprising a receiving unit configured to receive the echo signal from an object to which the ultrasonic waves are emitted.

* * * * *